(12) United States Patent
Kang et al.

(10) Patent No.: US 8,673,808 B2
(45) Date of Patent: Mar. 18, 2014

(54) CATALYST FOR HYDROCARBON STEAM CRACKING, METHOD OF PREPARING THE SAME AND METHOD OF PREPARING OLEFIN BY USING THE SAME

(71) Applicant: LG Chem, Ltd., Seoul (KR)

(72) Inventors: Jun-Han Kang, Daejeon (KR); Jonghun Song, Daejeon (KR); Junseon Choi, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 13/886,731

(22) Filed: May 3, 2013

(65) Prior Publication Data

US 2013/0244868 A1 Sep. 19, 2013

Related U.S. Application Data

(62) Division of application No. 12/793,855, filed on Jun. 4, 2010, now Pat. No. 8,481,451.

(30) Foreign Application Priority Data

Jun. 8, 2009 (KR) .................. 10-2009-0050333
Aug. 18, 2009 (KR) .................. 10-2009-0076145

(51) Int. Cl.
*B01J 27/224* (2006.01)
*B01J 23/00* (2006.01)

(52) U.S. Cl.
USPC ........... 502/308; 502/178; 502/256; 502/257; 502/263; 502/309; 502/311; 502/312; 502/313; 502/314; 502/315

(58) Field of Classification Search
USPC ................. 502/178, 256, 257, 263, 308, 309, 502/311–315
See application file for complete search history.

(56) References Cited

U.S. PATENT DOCUMENTS 2,336,783 A 12/1943 Fehrer
3,644,557 A 2/1972 Senes et al.
(Continued)

FOREIGN PATENT DOCUMENTS

CN 1416367 A 5/2003
CN 101353590 A 1/2009
(Continued)

OTHER PUBLICATIONS

Chinese Office Action for Application No. 201010199125.3 dated Jul. 2, 2012.
(Continued)

*Primary Examiner* — Cam N. Nguyen
(74) *Attorney, Agent, or Firm* — Lerner, David, Littenberg, Krumholz & Mentlik, LLP

(57) ABSTRACT

The present invention relates to a catalyst for hydrocarbon steam cracking, a method of preparing the same, and a method of preparing olefin by the hydrocarbon steam cracking by using the catalyst, and more specifically, to a catalyst for hydrocarbon steam cracking for preparing light olefin including an oxide catalyst ($0.5 \leq j \leq 120$, $1 \leq k \leq 50$, A is transition metal, and x is a number corresponding to the atomic values of Cr, Zr, and A and values of j and k) represented by $CrZr_jA_kO_x$, wherein the composite catalyst is a type that has an outer radius $r_2$ of 0.5R to 0.96R (where R is a radius of a cracking reaction tube), a thickness (t; $r_2-r_1$) of 2 to 6 mm, and a length h of $0.5r_2$ to $10r_2$, a method of preparing the same, and a method of preparing light olefins such as ethylene, propylene, etc., by performing the hydrocarbon steam cracking reaction in the presence of the composite catalyst. The present invention can provide catalysts for hydrocarbon steam cracking having high physical strength, excellent stability at high temperature, low non-activation due to coke, and improved yield and selectivity of light olefins.

7 Claims, 6 Drawing Sheets

(a)

(b)

(56) References Cited

U.S. PATENT DOCUMENTS

| | | | |
|---|---|---|---|
| 3,725,495 A * | 4/1973 | Wrisberg et al. | 585/414 |
| 3,839,485 A * | 10/1974 | Wrisberg et al. | 585/651 |
| 3,855,388 A | 12/1974 | Rosinski | |
| 3,945,946 A | 3/1976 | Hindin et al. | |
| 3,969,542 A | 7/1976 | Tomita et al. | |
| 4,111,793 A | 9/1978 | Kolombos et al. | |
| 4,269,737 A * | 5/1981 | Grenoble et al. | 502/204 |
| 4,613,700 A | 9/1986 | Maki et al. | |
| 5,206,203 A | 4/1993 | Schneider et al. | |
| 5,600,051 A | 2/1997 | Baker et al. | |
| 6,224,748 B1 * | 5/2001 | Chang et al. | 208/112 |
| 6,518,216 B1 | 2/2003 | Han et al. | |
| 7,026,263 B2 | 4/2006 | Le Van Mao et al. | |
| 7,067,706 B2 | 6/2006 | Wilmet et al. | |
| 7,217,678 B2 | 5/2007 | Rao et al. | |
| 7,232,780 B2 | 6/2007 | Zhu et al. | |
| 7,504,358 B2 | 3/2009 | Rao et al. | |
| 7,935,654 B2 * | 5/2011 | Choi et al. | 502/308 |
| 7,951,987 B2 * | 5/2011 | Choi et al. | 585/651 |
| 8,123,931 B2 * | 2/2012 | Kang et al. | 208/121 |
| 2003/0114688 A1 | 6/2003 | Weiguny et al. | |
| 2003/0180473 A1 | 9/2003 | Nishihara et al. | |
| 2005/0245387 A1 | 11/2005 | Zhu et al. | |
| 2009/0012340 A1 | 1/2009 | Choi et al. | |

FOREIGN PATENT DOCUMENTS

| | | |
|---|---|---|
| EP | 0212320 A2 | 3/1987 |
| JP | 11-199876 A | 7/1999 |
| KR | 10-0449965 | 12/2004 |
| KR | 2006-0055366 A | 5/2006 |
| KR | 2009-0002996 U | 3/2009 |
| RU | 1011236 | 1/2000 |
| WO | 2004105939 A1 | 12/2004 |

OTHER PUBLICATIONS

Office Action from Korean Application No. 10-2009-0076145 dated Sep. 28, 2011.

Sohn et al. "Surface Characterization of Chromium Oxide-Zirconium Catalyst" Langmuir 1993 9, 126-131.

Takita et al. "Catalytic decomposition of CFCs," Catalysis Surveys from Japan 2 (1998) 165-173.

* cited by examiner

CATALYST FOR HYDROCARBON STEAM CRACKING, METHOD OF PREPARING THE SAME AND METHOD OF PREPARING OLEFIN BY USING THE SAME

CROSS-REFERENCE TO RELATED APPLICATIONS

This application is a divisional of U.S. application Ser. No. 12/793,855 filed Jun. 4, 2010, now U.S. Pat. No. 8,481,451 which matured out of the above-identified application on Jul. 9, 2013, the present application which claims priorities from Korean Patent Application Nos. 10-2009-0050333 and 10-2009-0076145 filed on Jun. 8, 2009 and Aug. 18, 2009, respectively, in the Korean Intellectual Property Office, the disclosures of which are incorporated herein by reference in their entirety.

TECHNICAL FIELD

The present invention relates to a catalyst for hydrocarbon steam cracking for preparing light olefin, a method of preparing the same, and a method of preparing olefin by hydrocarbon steam cracking by using the catalyst, and more specifically, to a catalyst for hydrocarbon steam cracking, which has excellent thermal stability at high temperature, low non-activation due to coke, and improved yield and selectivity of light olefin, a method of preparing the same, and a method of preparing light olefin by using the catalyst.

BACKGROUND OF THE INVENTION

Ethylene and propylene, which are important raw materials of petrochemical products, are prepared by cracking hydrocarbon, which uses paraffin compound such as natural gas, naphtha, gas oil, etc., as main components, at a high temperature of at least 800° C. in the presence of a steam.

In the hydrocarbon steam cracking reaction, in order to increase the yield of ethylene and propylene, the conversion ratio of hydrocarbon should be increased or the selectivity of olefin should be increased. However, since there is a limitation in increasing the conversion ratio of hydrocarbon or the selectivity of olefin only by the pure steam cracking reaction, various methods capable of increasing the yield of olefin have been proposed.

In the hydrocarbon steam cracking reaction, there has been proposed the steam cracking method using a catalyst as the method capable of improving the yield of ethylene and propylene. U.S. Pat. No. 3,644,557 disclosed a method of using a catalyst made of magnesium oxide and zirconium oxide, U.S. Pat. No. 3,969,542 disclosed a method of using a catalyst including calcium aluminate as basic components, U.S. Pat. No. 4,111,793 disclosed manganese oxide carried in zirconium oxide, EP Laid-Open Patent No. 0212320 disclosed an iron catalyst carried in magnesium oxide, and U.S. Pat. No. 5,600,051 disclosed a catalyst made of barium oxide, alumina, and silica. In addition, PCT Patent No. 2004/105939 disclosed a method of using a catalyst made of potassium magnesium phosphate, silica, and alumina. However, in the case of using these catalysts, the catalyst material functions as a thermal medium in the carbon steam cracking reaction to improve the yield of olefin, however, is slight in the yield improvement of olefin as compared to the case of using a non-active carrier.

Russia Patent No. 1,011,236 disclosed a potassium vanadate catalyst formulated with boron oxide in an alumina carrier. However, in the case of using alkali metal oxide or potassium vanadate catalyst, the yield improvement of olefin by the catalyst becomes small as well as the loss of olefin essentially occurs at high temperature for hydrocarbon decomposition. In other words, the catalyst can exist in a liquid phase in the inside of a high-temperature cracking reactor due to a low melting point of catalyst components and the catalyst components are volatilized due to the fast flow of reaction gas to degrade the catalyst activation as the reaction time elapses.

U.S. Pat. No. 7,026,263 disclosed a method of using a hybrid catalyst made of molybdenum oxide, alumina, silica, silicalite, zirconium oxide, etc. Since the above-mentioned catalysts can be reacted at low reaction temperature, but is operated at very low hydrocarbon flux, it is difficult to directly apply the catalysts to the existing processes. In addition, the thermal stability of catalysts is significantly low at the reaction temperature of at least 700 to 800° C., such that the catalyst activation is lost.

In addition, since the existing cracking process is operated at high reaction temperature and high hydrocarbon linear velocity and generates a large amount of coke, the generated coke should be combusted at high temperature. In order to use the catalyst for a long time under the severe operation conditions, the catalysts should be stabilized against the thermal/physical deformations. The foregoing related arts have a problem in that the catalysts are vulnerable to the thermal/physical deformations or the stability thereof is not verified.

Therefore, in order to consider the economical efficiency of hydrocarbon steam cracking process and avoid the complexity of process, a need exists for a catalyst that significantly improves the yield and selectivity of light olefin and has excellent thermal/mechanical stability even at high temperature.

SUMMARY OF THE INVENTION

The present invention proposes to solve the above problem in the related art. The present invention provides a composite catalyst having a specific type including active component represented by $CrZr_jA_kO_x$ as a catalyst for hydrocarbon steam cracking, which has improved yield and selectivity of olefin, low non-activation due to coke, and excellent thermal stability at high temperature, when preparing olefin by cracking hydrocarbon with a steam and a method of preparing the same.

In addition, the present invention to provide a method of filling a composite catalyst for hydrocarbon steam cracking and a method of preparing light olefins by cracking hydrocarbon with a steam in the presence of the filled composite catalyst.

The present invention is described in detail hereinafter.

In order to achieve the above aspects, there is provided a composite catalyst for hydrocarbon steam cracking including an oxide catalyst ($0.5 \leq j \leq 120$, $1 \leq k \leq 50$, A is transition metal, and x is a number corresponding to the atomic values of Cr, Zr, and A and values of j and k) represented by $CrZr_jA_kO_x$, wherein the composite catalyst is a type that has an outer radius $r_2$ of 0.5R to 0.96R (where R is a radius of a cracking reaction tube), a thickness (t; $r_2-r_1$) of 2 to 6 mm, and a length h of $0.5r_2$ to $10r_2$.

In addition, there is provided a method of preparing a composite catalyst for hydrocarbon steam cracking including (a) mixing an oxide catalyst ($0.5 \leq j \leq 120$, $1 \leq k \leq 50$, A is transition metal, and x is a number corresponding to the atomic values of Cr, Zr, and A and values of j and k) represented by $CrZr_jA_kO_x$ and a carrier; (b) molding a mixture of the (a) in a specific type; and (c) sintering a molded object of the (b) and preparing the sintered molded object in a ring type that has an outer radius $r_2$ of 0.5R to 0.96R (where R is a radius of a cracking reaction tube), a thickness (t; $r_2-r_1$) of 2 to 6 mm, and a length h of $0.5r_2$ to $10r_2$.

Further, there is provided a method of preparing light olefins including cracking hydrocarbon with a steam in a reaction tube filled with the composite catalyst for hydrocarbon steam cracking according to the present invention.

Detailed Description of Main Elements

R: Radius of cracking reaction tube
$r_1$: Inner radius of ring
$r_2-r_1$: Thickness of ring
$r_2$: Outer radius of ring
h: Length of ring

DETAILED DESCRIPTION OF THE INVENTION

The advantages, features and aspects of the invention will become apparent from the following description of the embodiments with reference to the accompanying drawings, which is set forth hereinafter.

Hereinafter, the present invention will be described in detail.

When a composite catalyst that includes, as catalyst component, oxide including Cr and Zr and including one or more metal component selected from a group consisting of Ti, Nb, Mo, V, Co, Ni, W, Fe, and P and is molded in a specific type according to the present invention is prepared, the inventors confirmed that the composite catalyst has excellent catalyst activation to improve yield of light olefin, reduces non-activation due to coke, is thermally/mechanically stabilized even at high temperature not to cause deformations, thereby improving problems of degradation of hydrocarbon decomposition activation and yield of light olefin and completed the present invention based on this.

Composite Catalyst for Hydrocarbon Steam Cracking and a Method of Preparing the Same The composite catalyst for hydrocarbon steam cracking according to the present invention includes oxide defined by Formula 1 as catalyst component, wherein the composite catalyst has a type that has an outer radius $r_2$ of 0.5 R to 0.96 R (where R is a radius of a cracking reaction tube), a thickness (t; $r_2-r_1$) of 2 to 6 mm, and a length h of 0.5 $r_2$ to 10 $r_2$.

$$CrZr_jA_kO_x \quad \text{Formula 1}$$

In Formula 1, j is $0.5 \leq j \leq 120$, preferably $5 \leq j \leq 90$, and more preferably $70 \leq j \leq 90$, k is $1 \leq k \leq 50$, preferably $5 \leq k \leq 30$, and more preferably $15 \leq j \leq 28$, and x is a number corresponding to the atomic values of Cr, Zr, and A and values of j and k.

In addition, A is one or more metal component selected from a group consisting of Ti, Nb, Mo, V, Co, Ni, W, Fe, and P.

Figure 1:
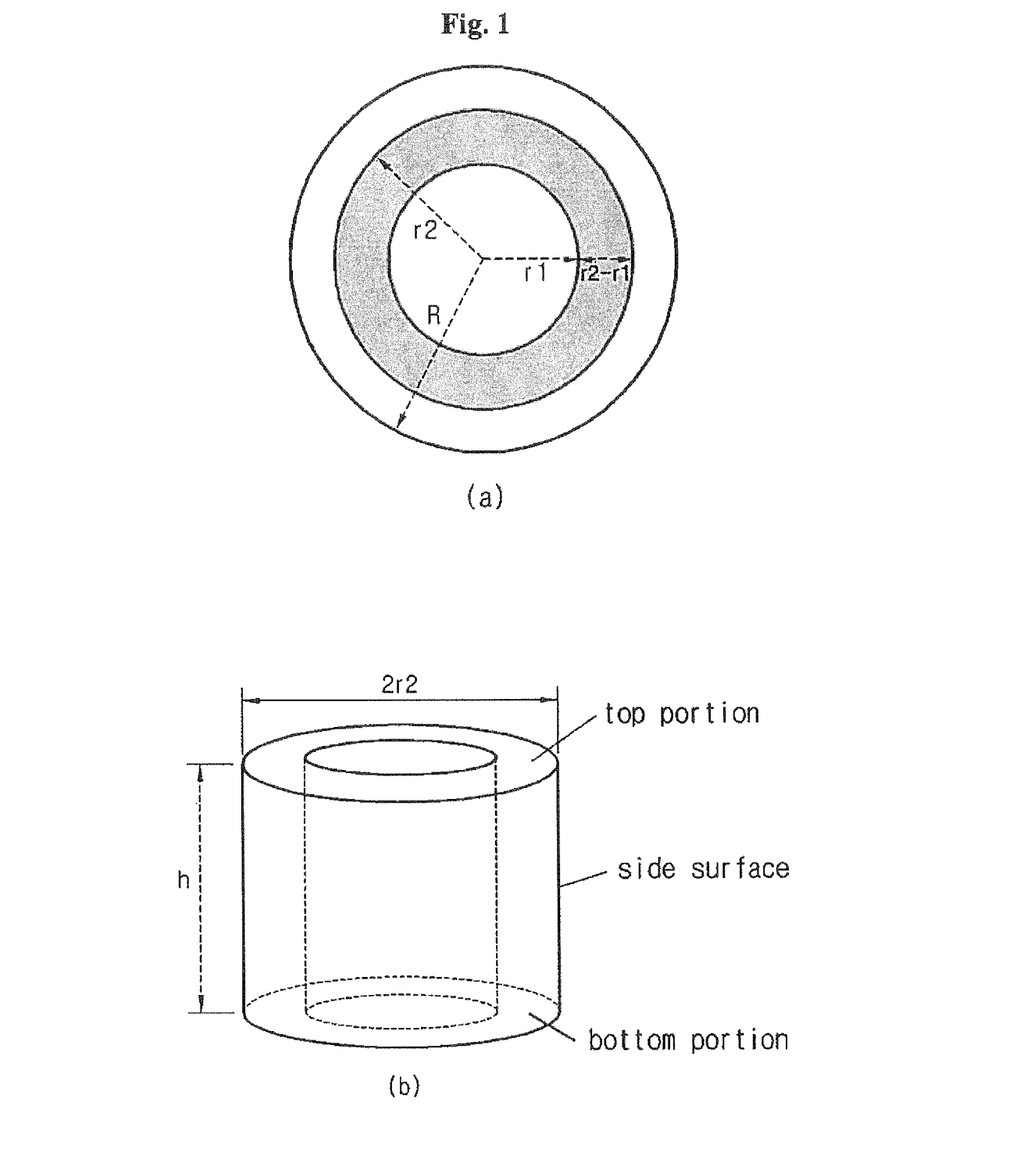
FIG. 1(a) is a top view of a shape of a composite catalyst for hydrocarbon steam cracking in a ring type, which is filled in a reaction tube in a row
FIG. 1(b) is a front view of the composite catalyst in a ring type.

FIG. 1(a) is a cross-sectional view of a cracking reaction tube filled with a composite catalyst according to the present invention and FIG. 1(b) shows a composite catalyst without holes as the composite catalyst according to the present invention.

When the composite catalyst is inserted into the cracking reaction tube having the radius R, it is preferable that a thickness t (that is, $r_2-r_1$) of the composite catalyst is in the range of 2 to 6 mm. Preferably, the outer radius $r_2$ has a value in the range of 0.5R to 0.96R and more preferably, has a value in the range of 0.5R to 0.75R. Further, a length h preferably has a value in the range of $0.5r_2$ to $10r_2$ and more preferably has a value in the range of $0.5r_2$ to $5r_2$.

When the thickness t (that is, $r_2-r_1$) of the composite catalyst is less than 2 mm, the composite catalyst can be crushed and when the thickness is more than 6 mm, the differential pressure in the cracking reaction tube increases and the residence time of reaction products further reduces to reduce the yield of olefin.

When the outer radius $r_2$ of the composite catalyst is less than 0.5 R, the composite catalysts are hard to fill in a row and when the outer radius $r_2$ is more than 0.96 R, the composite catalyst is hard to insert and is crushed due to deformations.

Moreover, when the length h of the composite catalyst is less than 0.5 $r_2$ or more than 10 $r_2$, gases inside and outside a heat exchanging medium are not sufficiently mixed.

Figure 3:
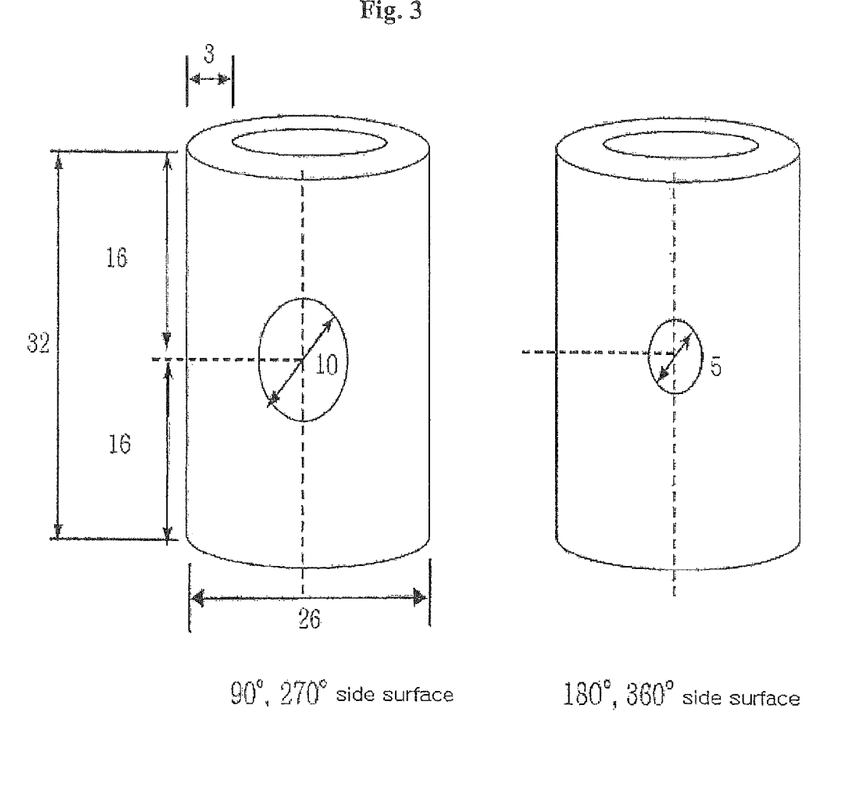
FIG. 3 shows a composite catalyst used in Example 2 as one example of the composite catalyst for hydrocarbon steam cracking in a ring type with holes according to the present invention.
Figure 4:
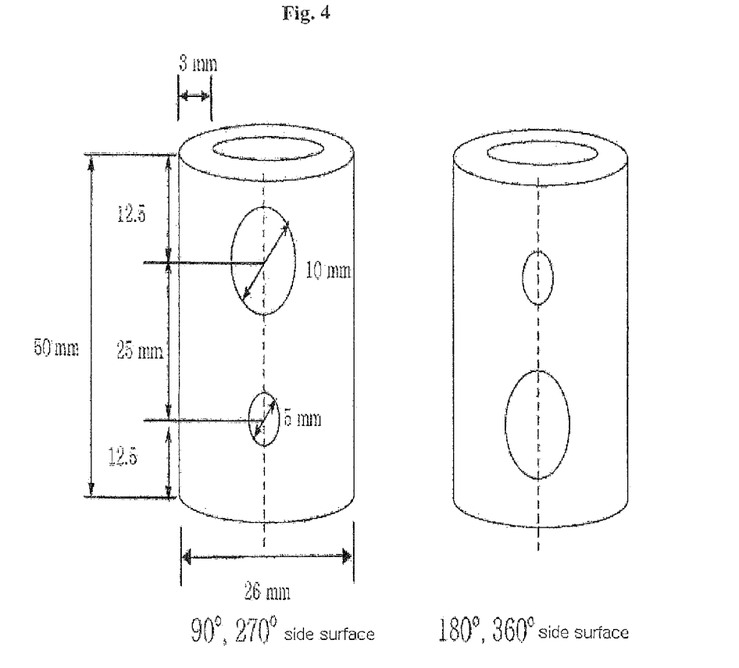
FIG. 4 shows a composite catalyst used in Example 3 as one example of the composite catalyst for hydrocarbon steam cracking in a ring type with holes according to the present invention.

In addition, the composite catalyst according to the present invention may be a ring type with holes as shown in FIGS. 3 and 4 so that the inside/outside fluids can be exchanged and mixed.

When fillers in a ring type are filled in the cracking reaction tube in a row, a 'channeling phenomenon', which the fluids inside and outside the ring are unevenly heated and decomposed while channels are separated, may occurs. This phenomenon cannot be solved since the mixing of fluids is insufficient only by open-cells existing in the fillers, but can be improved by forming holes so that the inside/outside fluids can be exchanged and mixed at an outer wall of the ring.

The hole is a circle, wherein a diameter of the circle is preferably 0.01 $r_2$ to 2 $r_2$. Preferably, at least two holes are formed at the outer wall of the ring in a length direction and a lateral direction, respectively. The diameter and number of holes may be changed. However, when there is a portion where the distance between the holes is reduced up to 3 mm, the strength of the ring is weak, such that the ring can be easily crushed. Therefore, the number of holes is not limited, but is preferably 2 to 50 and more preferably 2 to 10.

Moreover, since the differential pressure of the cracking reaction tube may be increased due to the existence of the holes, an area occupied by all the holes regarding the composite catalyst is not more than 50%. In order to reduce the increase in the differential pressure inside the reaction tube due to the holes, the ring without holes and the ring with holes can be mixed and filled.

When the composite catalyst of the present invention is filled in the cracking reaction tube, the filling rate is not more than 50% and is preferably in the range of 5 to 40%. When the filling rate is less than 5%, the increase in the yield of olefin is insignificant and when the filling rate is more than 40%, the residence time of the reaction gas reduces to degrade the yield of olefin.

The method of preparing compounds defined by Formula 1 includes: (a) preparing an aqueous solution by mixing water with Cr containing compound and a Zr containing compound or a Cr—Zr containing compound; (b) preparing a slurry by adding ammonia liquor to the prepared aqueous solution and co-precipitating them; (c) performing circulation heating or hydrothermal treatment on the prepared slurry; and (d) preparing an oxide catalyst defined by Formula 1 by filtering, drying, and burning the slurry.

The (a) includes preparing an aqueous solution by mixing water with metal compounds.

The Cr containing compound and the Zr containing compound or the Cr—Zr containing compound may be used in salt types, such as sulfates, nitrates, oxalates, halides, chlorides, etc. Preferably, the nitrates are used.

In addition, the metal compounds, that is, the Cr containing compound and the Zr containing compound or the Cr—Zr containing compound may be further mixed with third metal compound. As the third metal compound, one or more compound selected from a group consisting of Ti, Nb, Mo, V, Co, Ni, W, Fe, and P. Preferably, Ti, Ni, and P are used and more preferably, Ti and P are used.

The metal components of the third metal compounds may be used in types, such as salt, acid, oxide, hydroxide, alkoxide, etc. When the metal component of the third metal compound is an alkoxide precursor type, the alkoxide is hydrolyzed in water and thus, can be precipitated as salt in a solid state, such that strong acid such as nitric acid may be added to the alkoxide in order to dissolve the alkoxide.

The metal component of the third metal compound can be used by being dissolved in water and then mixed with Cr and Zr aqueous solution or can be used by being dissolved in water together with the Cr and Zr precursors.

The aqueous solution, in which the above-mentioned components are dissolved, is heated and agitated and at the same time, may be agitated for at least one hour so that it is sufficiently mixed in the range that the temperature of the aqueous solution is 40 to 80° C., preferably 60 to 70° C.

The (b) includes controlling pH to 7 to 9, preferably 8 to 8.5 by adding ammonia to the aqueous solution of the (a) and co-precipitating them to prepare slurry.

The (c) includes calculatedly heating the slurry of the (b) for at least 12 hours at the same temperature as the (a) or hydrothermally treating it at an autoclave in the range of 60 to 150° C.

The (d) includes filtering, drying, and burning the circulation-heated or hydrothermal-treated slurry of the step (c) to prepare a catalyst.

Preferably, the drying is performed for at least 2 hours at 120° C. Preferably, the burning is performed for at least 4 hours at 750 to 1600° C. When the burning is performed in the temperature range, the sintering is not rapidly made, such that the catalyst activation is not lost.

In addition, the method of preparing a composite catalyst for hydrocarbon steam cracking includes: (a) mixing an oxide catalyst component defined by Formula 1 with a carrier; (b) molding the mixture of the (a) in a specific type; and (c) sintering the molded object of the (b) to prepare the sintered molded object in a ring type that has an outer radius $r_2$ of 0.5R to 0.96R (where R is a radius of a cracking reaction tube), a thickness (t; $r_2-r_1$) of 2 to 6 mm, and a length h of $0.5r_2$ to $10r_2$.

The (a) includes mixing the oxide catalyst component defined by Formula 1 with the carrier.

Preferably, in the hydrocarbon steam cracking reaction, the catalyst component is mixed by 0.5 to 50 wt % based on the entire weight of the composite catalyst. When the catalyst component is mixed less than 0.5 wt %, it is difficult to exhibit the performance as the catalyst and when the catalyst component is mixed more than 50 wt %, the strength of the catalyst is weak. At the mixing the catalyst component with the carrier, a binder may be further mixed.

Examples of the carrier may include general carriers, such as alpha alumina, silica, silica-alumina, zirconium oxide, magnesium oxide, magnesium aluminate, calcium aluminate, silicon carbide, aluminum titanate, zeolite, etc. Preferably, silicon carbide as a carrier is used. When the silicon carbide is used as a carrier, silicon and carbon, which are precursors of the silicon carbide, may be mixed with the catalyst component. At this time, the sintering process of the (c) is performed, such that silicon and carbon is converted into silicon carbide.

The silicon carbide has a stabilized structure at high temperature of at least 1000° C., has large thermal impact, carburization, and creep resistance, has low coke deposition, and has large thermal conductivity, such that it becomes a thermal transfer medium suitable for the cracking reaction. When the silicon carbide is used, the crushing due to impact can be prevented and the amount of carbon deposit can be reduced.

The (b) includes performing a molding in order to make the mixture of the (a) in a specific type. In other words, the (b) includes performing a compression molding or an extrusion molding. Herein, as the molding type of the composite catalyst, several specific types may be used, but preferably, a ring type is used.

In addition, holes may be formed at the outer wall of the composite catalyst according to the present invention (FIGS. 3 and 4). The hole is a circle, wherein a diameter of the circle is preferably $0.01 r_2$ to $2 r_2$. Preferably, at least two holes are formed at the outer wall of the ring in a length direction and a lateral direction, respectively. The number of holes is not limited, but is preferably 2 to 50 and more preferably 2 to 10.

At this time, examples of methods for preparing the composite catalyst for hydrocarbon steam cracking having holes may include a method of making the composite catalyst in a ring type, sintering them, and then forming holes at an outer wall, a method of making a mold type in a ring type with holes when performing the extrusion molding at the (b), injecting carrier catalyst component in the mold, pressing it to prepare the composite catalyst, and then sintering the composite catalyst, etc., may be used, but are not limited thereto.

The (c) includes sintering molding having a specific type of the (b). The molding of the (b) is subjected to the sintering process, which reduces the volume of the molding. Therefore, the molding is prepared as the composite catalyst having desired size, density, and surface area. At this time, the composite catalyst according to the present invention is prepared in a ring type that has an outer radius $r_2$ of 0.5 R to 0.96 R (where R is a radius of a cracking reaction tube), a thickness (t; $r_2-r_1$) of 2 to 6 mm, and a length h of 0.5 $r_2$ to 10 $r_2$.

When the outer radius of the composite catalyst is less than 0.5 R, the composite catalysts are hard to fill in a row and when the outer radius $r_2$ is more than 0.96 R, the composite catalyst is hard to insert and is crushed due to the deformations of the reaction tube at high temperature. Moreover, when the thickness of the composite catalyst is less than 2 mm, the composite catalyst can be crushed and when the thickness is more than 6 mm, the differential pressure in the cracking reaction tube increases and the residence time of reaction products further reduces to reduce the yield of olefin. Further, when the length of the composite catalyst is less than 0.5 $r_2$, the composite catalysts are hard to fill in a row and when the length is more than 10 $r_2$, the differential pressure is largely increased when the crushing is performed.

Preferably, the sintering is performed for at least 2 hours, preferably 6 to 24 hours at a temperature of at least 1200° C., preferably at a temperature of 800 to 2000° C.

As described above, the sintered composite catalyst is preferably prepared to have a density of 0.5 to 3.5 g/cm$^3$, up to 50 m$^2$/g surface area, and compression strength of at least 1000 N.

Examples of the reactor applicable to the hydrocarbon steam cracking reaction may include a fixed bed reactor, a fluidized bed reactor, a moving bed reactor, etc. In particular, when the fixed bed reactor is used, the catalyst molded in a sphere type or a pellet type may be used, but has a problem in that the differential pressure is largely formed in a catalyst layer. To solve this problem, it is preferable that the catalysts molded in specific types such as a ring type, a pipe type, a tube type, etc., are filled in a row in order to maximally reduce the filling rate of the catalyst layer.

At least one composite catalyst is inserted into the cracking reaction tube according to the length. In some cases, the composite catalyst is separated into several ten to several hundred, which may be filled in the reaction tube in a row.

In addition, the composite catalyst for hydrocarbon steam cracking according to the present invention may be prepared to having many huge pores.

At the (a) of the method of preparing a composite catalyst for hydrocarbon steam cracking, if organic polymer compound is mixed together when the oxide catalyst component defined by Formula 1 and the carrier powder are mixed, many huge pores are generated inside the composite catalyst while the organic polymer material is decomposed at the (c).

Preferably, examples of the organic polymer material may include high density polyethylene (HDPE), polymethylmethacrylate (PMMA), polyvinylalcohol (PVA), starch, etc. Preferably, the particle size of the polymer material is in the range of 2 to 600 μm and 1 to 20 parts by weight for every part by weight of the catalyst component and the carrier powder is mixed.

Method of Preparing Olefin Using the Composite Catalyst

A method of preparing light olefins according to the present invention includes cracking hydrocarbon with a steam using the composite catalyst for hydrocarbon steam cracking according to the above mentioned method.

When the composite catalyst according to the present invention is applied as a catalyst for hydrocarbon steam cracking, the reaction yield can be improved, the selectivity of light olefins, in particular, propylene can be improved, and the thermal stability can be increased.

The light olefin according to the present invention means olefin having up to 4 carbon atoms and in particular, may include ethylene, propylene, etc.

The hydrocarbon steam cracking reaction for preparing the light olefin may be performed under the conditions that reaction temperature is 600 to 1000° C., a weight ratio of steam to hydrocarbon is 0.3 to 1.0, and space velocity (LHSV) is 1 to 20 hr$^{-1}$.

In the reaction, examples of the applicable reactor may include a fixed bed reactor, a fluidized bed reactor, a moving bed reactor, etc. In particular, when the fixed bed is used, the catalyst molded in the sphere type or the pellet type may be used and has a problem in that the differential pressure is largely formed in a catalyst layer. Using the composite catalyst for hydrocarbon steam cracking according to the present invention can maximally increase the porosity of the catalyst layer, making it possible to solve the above problem.

The present invention will be described in detail with reference to the following examples. However, these examples are illustrated by way of example only and the technical scope of the present invention is not limited thereto.

EXAMPLES

Example 1

Figure 2:
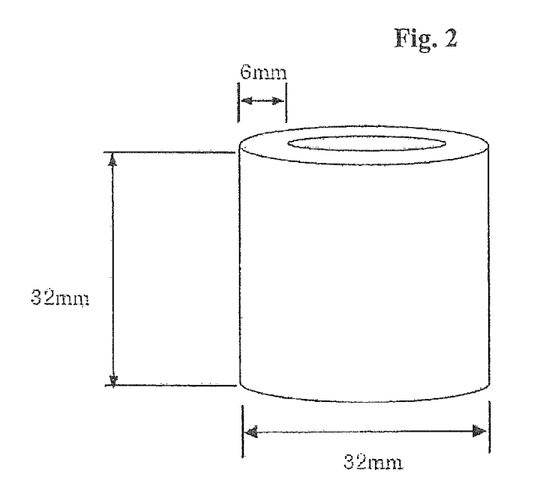
FIG. 2 shows a composite catalyst used in Example 1 as one example of the composite catalyst for hydrocarbon steam cracking in a ring type without holes according to the present invention.

A composite catalyst in a type as shown in FIG. 2 was prepared by mixing and sintering 10 wt % of CrZr$_{83.3}$Ti$_{16.7}$O$_x$ and 90 wt % silicon carbide and then filled in a reaction tube having a diameter of 4.3 cm and a length of 300 cm in a row. At this time, the filling rate is 32.9%.

Example 2

A composite catalyst in a type as shown in FIG. 3 was prepared by mixing and sintering 10 wt % of CrZr$_{83.3}$Ti$_{16.7}$O$_x$ and 90 wt % silicon carbide and then filled in a reaction tube having a diameter of 4.3 cm and a length of 300 cm in a row. At this time, the filling rate is 13.1%.

Example 3

A composite catalyst in a type as shown in FIG. 4 was prepared by mixing and sintering 5 wt % of CrZr$_{83.3}$Ti$_{16.7}$O$_x$ and 95 wt % silicon carbide and then filled in a reaction tube having a diameter of 4.3 cm and a length of 300 cm in a row. At this time, the filling rate is 12.7%.

Comparative Example 1

Hydrocarbon steam cracking was performed in an empty reaction tube having a diameter of 4.3 cm and a length of 300 cm in which the composite catalyst was not filled.

Experimental Example

In the state where the composite catalyst of Examples 1 to 3 is filled or in the state where the composite catalyst is not filled (comparative example 1), ethylene and propylene were prepared in the following methods.

At this time, in the steam contact cracking reaction of hydrocarbon, naphtha was used as hydrocarbon and the composition and physical properties of the used naphtha are as follows.

TABLE 1

| Physical Properties | | | | | | |
|---|---|---|---|---|---|---|
| | | | Composition (wt %) | | | |
| Density (g/cc) | Initial boiling point (° C.) | Terminal Boiling Point (° C.) | n-paraffin | 1-paraffin | Naphthene | Aromatic |
| 0.675 | 30.9 | 160.7 | 39.5 | 38.9 | 15.3 | 6.3 |

The naphtha and water, which are reactions, were injected into a reactor by a metering pump. At this time, the injection ratio of naphtha and water became 2:1 based on weight ratio and the flux of naphtha was controlled so that LHSV is 10 hr$^{-1}$. The naphtha and water injected into the reactor were mixed via each vaporizer, passed through a primary preheater heated at 550° C., passed through a secondary preheater heated at 650° C., and then injected into the reactor (300 cm in length and 4.3 cm in diameter).

The contact cracking reaction occurred while the mixture of steam naphtha via the secondary preheater passes through the reactor heated by an electric furnace. At this time, the electric furnace, which is a heat source, was changed between 940 to 1060° C. and the outlet temperature (reaction temperature) was changed between 740 to 830° C.

Water and heavy oil were condensed and separated in a liquid phase while the reaction products passes through two condensers connected in series and the remaining gaseous mixtures were analyzed by a gas chromatography connected in on-line and then discharged.

After the above-mentioned naphtha contact decomposition process is maintained for about 120 hours, coke was combusted and regenerated under an atmosphere of 800° C. steam-air.

The yield of ethylene was calculated by the following Mathematical Formula 1 and the yield of other products (propylene) was calculated in the same manner.

Yield of ethylene (wt %)=ethylene generation amount/naphtha injection amount×100.   Mathematical Formula 1 hydrocarbon decomposition activation is further increased at the same heat source temperature to increase the yield of ethylene and propylene as compared to Example 1. In addition, the selectivity of propylene was increased to largely increase the yield of propylene as compared to Example 1 (FIG. 5) Therefore, the ratio of ethylene to propylene was reduced as compared to Example 1.

Figure 6:
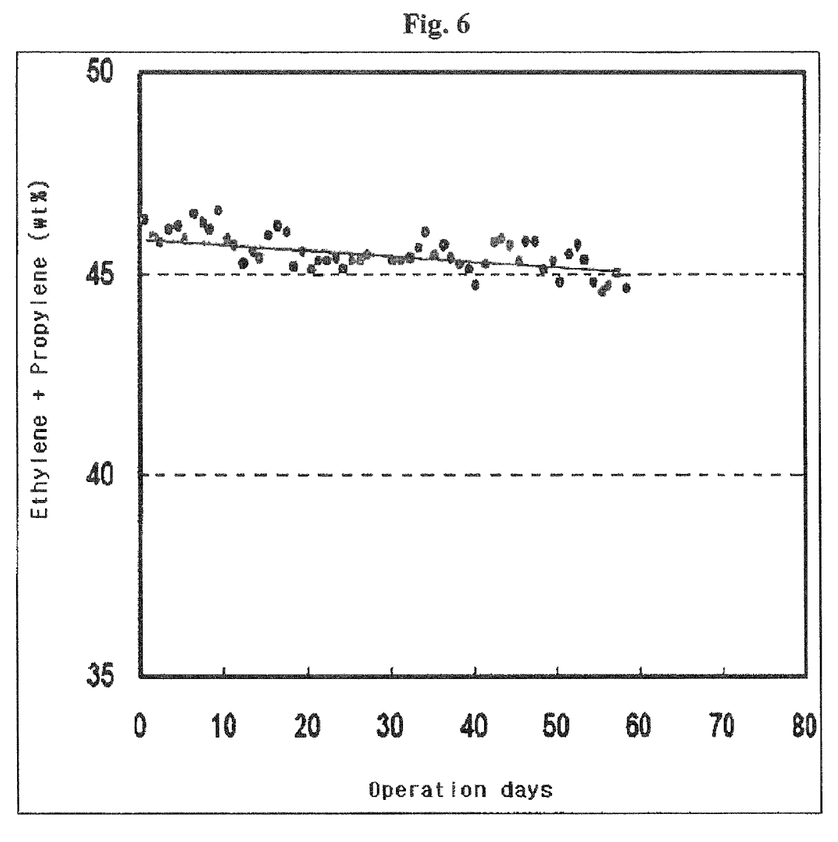
FIG. 6 shows yield of ethylene and propylene that are products according to an operation time when the composite catalyst according to Example 3 is used as a catalyst in the hydrocarbon steam cracking reaction according to the present invention.

Moreover, when the composite catalyst according to Example 3 having the outer radius of $r_2$=0.6 R and having eight holes on the side surfaces thereof to reduce the filling rate is filled, the hydrocarbon decomposition activation as well as the selectivity of propylene is further increased as compared to Example 2. Example 3 reduces the non-activation due to coke when being operated for a long time and is thermally/mechanically stabilized not to suddenly increase the differential pressure due to the crushing during the operation (FIG. 6)

As described above, the present invention provides the composite catalyst for hydrocarbon steam cracking that has excellent thermal/mechanical stability at high temperature, low non-activation due to coke, and improved yield and selectivity of light olefins.

While the present invention has been described with respect to the specific embodiments, it will be apparent to those skilled in the art that various changes and modifications may be made without departing from the spirit and scope of the invention as defined in the following claims.

TABLE 2

| | Heat source Temperature (° C.) | Outlet reaction temperature (° C.) | Yield of products (wt %) | | Ratio of Ethylene/to Propylene |
|---|---|---|---|---|---|
| | | | Ethylene | Propylene Ethylene + Propylene | |
| Comparative Example 1 | 980 | 766 | 22.69 | 16.57 | 39.26 | 1.37 |
| | 1000 | 778 | 24.26 | 16.29 | 40.55 | 1.49 |
| | 1020 | 787 | 25.89 | 16.16 | 42.05 | 1.60 |
| | 1040 | 797 | 27.75 | 15.91 | 43.66 | 1.74 |
| | 1060 | 812 | 29.31 | 14.48 | 43.79 | 2.02 |
| Example 1 | 940 | 763 | 19.79 | 15.89 | 35.68 | 1.25 |
| | 960 | 777 | 22.03 | 16.02 | 38.05 | 1.38 |
| | 980 | 791 | 24.81 | 16.13 | 40.94 | 1.54 |
| | 1000 | 804 | 26.6 | 15.78 | 42.38 | 1.69 |
| | 1020 | 821 | 29.51 | 14.62 | 44.13 | 2.02 |
| Example 2 | 940 | 758 | 21.01 | 16.62 | 37.63 | 1.26 |
| | 960 | 775 | 23.29 | 17.13 | 40.42 | 1.36 |
| | 980 | 789 | 25.47 | 17.22 | 42.69 | 1.48 |
| | 1000 | 806 | 27.8 | 16.93 | 44.73 | 1.64 |
| | 1020 | 824 | 29.51 | 15.83 | 45.34 | 1.86 |
| Example 3 | 960 | 777 | 25.67 | 17.35 | 43.02 | 1.48 |
| | 980 | 792 | 27.74 | 17.06 | 44.8 | 1.63 |
| | 1000 | 808 | 29.25 | 16.28 | 45.53 | 1.80 |
| | 1020 | 824 | 31.14 | 14.76 | 45.9 | 2.11 |

Figure 5:
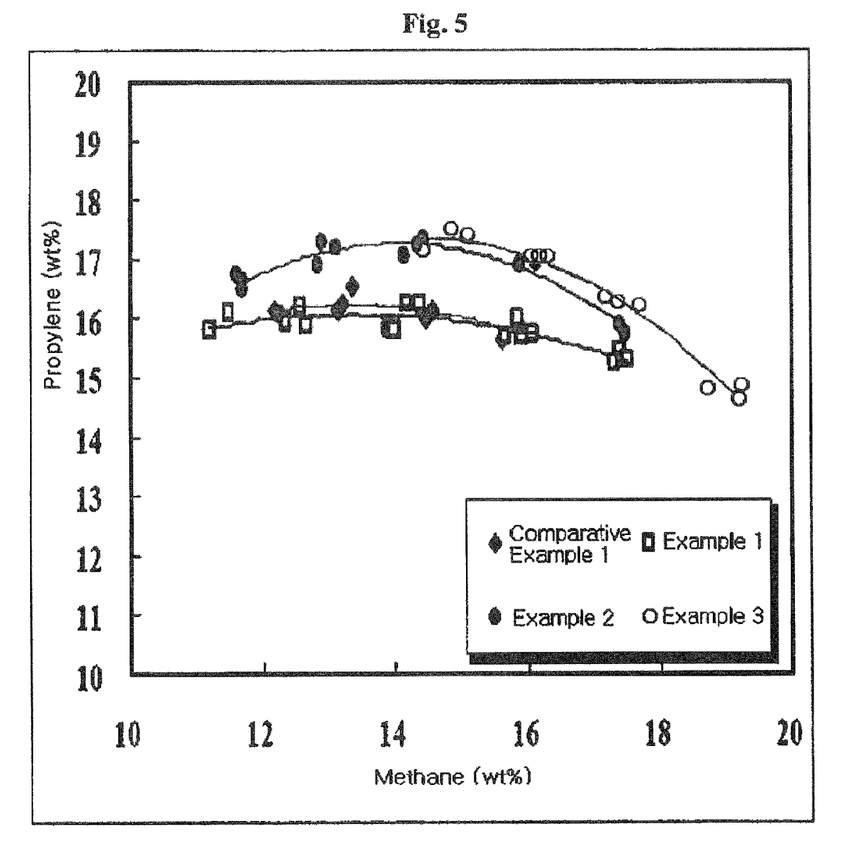
FIG. 5 shows a ration of methane/propylene according to reaction temperature in the case where the composite catalyst according to Examples 1 to 3 is used as a catalyst in the hydrocarbon steam cracking reaction according to the present invention and in the case of Comparative Example 1 that does not use the catalyst.

As can be appreciated from Table 2, when the composite catalyst in a ring type having the outer radius of $r_2$=0.74R and not having holes is filled (Example 1), the hydrocarbon decomposition activation was increased to increase the yield of ethylene as well as the ratio of ethylene to propylene was at the same heat source temperature as compared to Comparative Example 1, but the selectivity of propylene was the same as Comparative Example 1 (FIG. 5).

When the composite catalyst according to Example 2 having the outer radius of $r_2$=0.6R and having four holes on the side surfaces thereof to reduce the filling rate is filled, the

What is claimed is:

1. A method of preparing a composite catalyst for hydrocarbon steam cracking comprising:
   (a) mixing an oxide catalyst (0.5≤j≤120, 1≤k≤50, A is transition metal, and x is a number corresponding to the atomic values of Cr, Zr, and A and values of j and k) represented by $CrZr_jA_kO_x$ and a carrier;
   (b) molding a mixture of the (a); and
   (c) sintering a molded object obtained in (b) wherein the obtained composite catalyst has a ring shape that has an outer radius $r_2$ of 0.5R to 0.96R (where R is a radius of a cracking reaction tube), a thickness (t; outer radius $r_2$–inner radius $r_1$) of 2 to 6 mm, and a length (h) of $0.5r_2$ to $10r_2$.

2. The method of preparing a composite catalyst for hydrocarbon steam cracking of claim 1, wherein the oxide catalyst is mixed with the carrier in the (a) together with one or more organic polymer material selected from a group consisting of high density polyethylene (HDPE), polymethylmethacrylate (PMMA), polyvinylalcohol (PVA) and starch.

3. The method of preparing a composite catalyst for hydrocarbon steam cracking of claim 2, wherein a particle size of the organic polymer compound is 2 to 600 μm.

4. The method of preparing a composite catalyst for hydrocarbon steam cracking of claim 1, wherein the (c) is performed for 6 to 24 hours at a temperature of 800 to 2000° C.

5. The method of preparing a composite catalyst for hydrocarbon steam cracking of claim 1, wherein the oxide catalyst is mixed by 0.5 to 50 wt % based on the total weight of the composite catalyst.

6. The method of preparing a composite catalyst for hydrocarbon steam cracking of claim 1, wherein the composite catalyst molded at the (b) is a shape with holes, the hole being a circle and a diameter of the circle being $0.01r_2$ to $2r_2$.

7. The method of preparing a composite catalyst for hydrocarbon steam cracking of claim 1 wherein the carrier is one or more selected from the group consisting of alpha alumina, silica, silica-alumina, zirconium oxide, magnesium oxide, magnesium aluminate, calcium aluminate, silicon carbide, aluminum titanate, and zeolite.

* * * * *